(12) United States Patent
Shalev et al.

(10) Patent No.: US 11,712,560 B2
(45) Date of Patent: Aug. 1, 2023

(54) COSMETIC SKIN REJUVENATION

(71) Applicant: POLLOGEN LTD., Tel Aviv-Jaffa (IL)

(72) Inventors: Pinchas Shalev, Herzeliya (IL); Zion Azar, Shoham (IL)

(73) Assignee: Pollogen Ltd., Tel Aviv (IL)

( * ) Notice: Subject to any disclaimer, the term of this patent is extended or adjusted under 35 U.S.C. 154(b) by 29 days.

(21) Appl. No.: 17/713,785

(22) Filed: Apr. 5, 2022

(65) Prior Publication Data

US 2022/0226644 A1 Jul. 21, 2022

Related U.S. Application Data

(60) Continuation of application No. 17/676,125, filed on Feb. 19, 2022, which is a continuation of application
(Continued)

(51) Int. Cl.
*A61N 1/20* (2006.01)
*A61B 18/12* (2006.01)
(Continued)

(52) U.S. Cl.
CPC ............ *A61N 1/20* (2013.01); *A45D 44/22* (2013.01); *A61B 18/1206* (2013.01);
(Continued)

(58) Field of Classification Search
CPC ........ A45D 44/22; A61N 1/20; A61N 1/0502; A61N 1/205; A61N 1/403; A61B 18/18;
(Continued)

(56) References Cited

U.S. PATENT DOCUMENTS 2,444,173 A 6/1948 St. Pierre
3,297,024 A 1/1967 Robinson
(Continued)

FOREIGN PATENT DOCUMENTS

CN 1721010 1/2006
EP 1568395 8/2005
(Continued)

OTHER PUBLICATIONS

Godfrey, Sheila, "10 Electricity" In: "Principles and Practice of Electrical Epilation", Oct. 16, 2001, Butterworth Heinemann, pp. 75-83.
(Continued)

*Primary Examiner* — Khadijeh A Vahdat
*Assistant Examiner* — Yasamin Ekrami
(74) *Attorney, Agent, or Firm* — ISUS Intellectual Property PLLC; Anthony Jason Mirabito

(57) ABSTRACT

A cosmetic method for treating a skin of a person is presented, the method comprises inserting one or more needles to one or more depths into the skin of the person such that at least a tip of at least one needle of the one or more needles is deployed within a muscle layer of the person's skin; applying a negative DC voltage to the one or more needles, while a skin of the person is in contact with a positive electrode to form one or more closed circuits of DC current through the person's body; and providing the DC current for a pre-selected amount of time to damage and/or ablate muscles and/or muscle nerve cells in the muscle layer; thereby providing a skin treatment comprising reducing and/or smoothing wrinkles from the person's skin.

17 Claims, 8 Drawing Sheets

Related U.S. Application Data

No. 15/422,557, filed on Feb. 2, 2017, now abandoned, which is a division of application No. 13/388,521, filed as application No. PCT/IL2010/000583 on Jul. 21, 2010, now Pat. No. 9,596,920.

(60) Provisional application No. 61/231,033, filed on Aug. 4, 2009.

(51) Int. Cl.

| | | |
|---|---|---|
| *A61N 1/05* | (2006.01) | |
| *A45D 44/22* | (2006.01) | |
| *A61B 18/14* | (2006.01) | |
| *A61N 1/40* | (2006.01) | |
| *A61B 18/18* | (2006.01) | |
| *A61B 17/00* | (2006.01) | |
| *A61B 18/00* | (2006.01) | |

(52) U.S. Cl.
CPC ........ *A61B 18/1477* (2013.01); *A61N 1/0502* (2013.01); *A61N 1/205* (2013.01); *A61N 1/403* (2013.01); *A61B 18/18* (2013.01); *A61B 2017/00761* (2013.01); *A61B 2018/0047* (2013.01); *A61B 2018/00077* (2013.01); *A61B 2018/00452* (2013.01); *A61B 2018/00589* (2013.01); *A61B 2018/00595* (2013.01); *A61B 2018/00875* (2013.01); *A61B 2018/00994* (2013.01); *A61B 2018/1266* (2013.01); *A61B 2018/143* (2013.01); *A61B 2018/1425* (2013.01); *A61B 2218/002* (2013.01); *A61B 2218/007* (2013.01)

(58) Field of Classification Search
CPC .......... A61B 2017/00761; A61B 2018/00077; A61B 2018/00452; A61B 2018/0047; A61B 2018/00589; A61B 2018/00595; A61B 2018/00875; A61B 2018/00994; A61B 2018/1266; A61B 2018/1425; A61B 2018/143; A61B 18/1206; A61B 18/1477; A23V 2300/12

See application file for complete search history.

(56) References Cited

U.S. PATENT DOCUMENTS

| | | | |
|---|---|---|---|
| 4,702,732 | A | 10/1987 | Powers et al. |
| 5,169,398 | A | 12/1992 | Glaros |
| 5,296,683 | A | 3/1994 | Burkett et al. |
| 5,419,344 | A | 5/1995 | DeWitt |
| 5,476,504 | A | 12/1995 | Paolizzi |
| 5,562,706 | A | 10/1996 | Lauterbach |
| 5,755,753 | A | 5/1998 | Knowlton |
| 5,797,904 | A | 8/1998 | Smith |
| 5,797,966 | A | 8/1998 | Bontoux |
| 5,961,475 | A | 10/1999 | Guity |
| 6,139,545 | A * | 10/2000 | Utley ................. A61B 18/1233 606/41 |
| 6,273,884 | B1 | 8/2001 | Altshuler et al. |
| 6,277,116 | B1 * | 8/2001 | Utely ................... A61B 18/14 606/41 |
| 6,425,912 | B1 | 7/2002 | Knowlton |
| 6,546,934 | B1 | 4/2003 | Ingle et al. |
| 6,692,490 | B1 | 2/2004 | Edwards |
| 6,840,954 | B2 | 1/2005 | Dietz et al. |
| 7,953,500 | B2 | 5/2011 | Bingham et al. |
| 9,596,920 | B2 | 3/2017 | Shalev et al. |
| 2001/0014815 | A1 | 8/2001 | Matsumura et al. |
| 2002/0032441 | A1 | 3/2002 | Ingle |
| 2002/0120260 | A1 | 8/2002 | Morris et al. |
| 2003/0032950 | A1 | 2/2003 | Altshuler |
| 2003/0187488 | A1 | 10/2003 | Kreindel |
| 2004/0019350 | A1 | 1/2004 | O'Brien |
| 2004/0073079 | A1 | 4/2004 | Altshuler |
| 2004/0220622 | A1 | 11/2004 | Bernabei |
| 2005/0015085 | A1 | 1/2005 | McClurken et al. |
| 2005/0107832 | A1 | 5/2005 | Bernabei |
| 2005/0154433 | A1 | 7/2005 | Levy |
| 2005/0171583 | A1 | 8/2005 | Mosher |
| 2005/0222565 | A1 * | 10/2005 | Manstein ............... A61M 5/158 606/41 |
| 2006/0036300 | A1 | 2/2006 | Kreindel |
| 2006/0089688 | A1 * | 4/2006 | Panescu ............ A61B 18/1477 607/101 |
| 2006/0205996 | A1 | 9/2006 | Presthus |
| 2006/0206103 | A1 | 9/2006 | Altshuler |
| 2006/0206110 | A1 | 9/2006 | Knowlton et al. |
| 2006/0217704 | A1 | 9/2006 | Cockburn et al. |
| 2007/0055154 | A1 | 3/2007 | Torbati |
| 2007/0055180 | A1 | 3/2007 | Deem |
| 2007/0060989 | A1 | 3/2007 | Deem |
| 2007/0179490 | A1 | 8/2007 | Azar |
| 2007/0198004 | A1 | 8/2007 | Altshuler |
| 2007/0232966 | A1 | 10/2007 | Applebaum et al. |
| 2008/0039914 | A1 * | 2/2008 | Cory .................... A61N 1/0551 607/116 |
| 2008/0103565 | A1 | 5/2008 | Altshuler et al. |
| 2008/0215039 | A1 | 9/2008 | Slatkine |
| 2008/0312646 | A9 | 12/2008 | Peterson |
| 2009/0043293 | A1 | 2/2009 | Pankratov |
| 2009/0156958 | A1 | 6/2009 | Mehta et al. |
| 2009/0270963 | A1 | 10/2009 | Pelger |
| 2010/0016850 | A1 | 1/2010 | Ron Edoute |
| 2010/0049186 | A1 | 2/2010 | Ingle et al. |
| 2010/0057149 | A1 | 3/2010 | Fahey |
| 2010/0174137 | A1 | 7/2010 | Shim |
| 2010/0228304 | A1 | 9/2010 | Kriksunov et al. |
| 2011/0009692 | A1 | 1/2011 | Gross |
| 2011/0130618 | A1 | 6/2011 | Ron Edoute |
| 2011/0224665 | A1 | 9/2011 | Crosby et al. |
| 2011/0230931 | A1 | 9/2011 | Hagege |
| 2012/0215141 | A1 | 8/2012 | Peddicord |
| 2012/0027120 | A1 | 10/2012 | Shalev et al. |
| 2012/0271206 | A1 | 10/2012 | Shalev et al. |
| 2013/0018222 | A1 | 1/2013 | Miroshnichenko |
| 2015/0164401 | A1 | 6/2015 | Toth |
| 2015/0297908 | A1 | 10/2015 | Minsod |
| 2016/0121112 | A1 | 5/2016 | Zion |
| 2016/0263387 | A1 | 9/2016 | Minsod |
| 2016/0346561 | A1 | 12/2016 | Ron Edoute |
| 2016/0346568 | A1 | 12/2016 | Rockweiler |
| 2017/0014395 | A1 | 5/2017 | Shalev et al. |
| 2017/0143997 | A1 | 5/2017 | Rockweiler |
| 2017/0023946 | A1 | 8/2017 | Shalev et al. |
| 2021/0002336 | A1 | 1/2021 | Shalev et al. |
| 2022/0018438 | A1 | 6/2022 | Shalev et al. |
| 2022/0022664 | A1 | 7/2022 | Shalev et al. |
| 2022/0226646 | A1 | 7/2022 | Shalev et al. |
| 2022/0226647 | A1 | 7/2022 | Shalev et al. |
| 2022/0226648 | A1 | 7/2022 | Shalev et al. |
| 2022/0226649 | A1 | 7/2022 | Shalev et al. |
| 2022/0233851 | A1 | 7/2022 | Shalev et al. |
| 2022/0028078 | A1 | 9/2022 | Shalev et al. |

FOREIGN PATENT DOCUMENTS

| | | |
|---|---|---|
| EP | 2476460 | 7/2012 |
| GB | 277882 | 9/1927 |
| JP | H119703 | 1/1999 |
| JP | 3041670 | 5/2000 |
| JP | 2001259047 | 9/2001 |
| JP | 2003010145 | 1/2003 |
| JP | 2003019215 | 1/2003 |
| JP | 2004522497 | 7/2004 |
| JP | 2007507317 | 3/2007 |
| JP | 2006520247 | 9/2007 |
| JP | 2008173231 | 7/2008 |
| JP | 2008537896 | 10/2008 |
| JP | 2008545462 | 12/2008 |
| JP | 2012065693 | 4/2012 |
| RU | 2153366 | 7/2000 |

(56) References Cited

FOREIGN PATENT DOCUMENTS

| | | |
|---|---|---|
| RU | 2005131621 | 2/2006 |
| WO | 0112089 | 2/2001 |
| WO | WO-0112089 A1 * | 2/2001 ......... A61B 18/1477 |
| WO | 2008058452 | 5/2008 |
| WO | 2009023568 | 2/2009 |
| WO | 2012080394 | 6/2012 |
| WO | 2015014811 | 2/2015 |

OTHER PUBLICATIONS

Search Report—Corresponding European Application No. 10806137.5, dated Aug. 26, 2016, 12 pages.
Office Action for Russian Application No. 2012107673 dated Aug. 8, 2014.
Office Action for Japanese Application No. 2012523428 dated Sep. 16, 2014.
International Search Report of Application No. PCT/IL2010/000583, dated Nov. 29, 2010.
Godfrey, Sheila, "10 Electricity" In: "Principlesand Practice of Electricall Epilation", Oct. 16, 2001, Butterworth Heinemann, pp. 75-83.
Y.Y. Dribnokhod, Cosmetology, Rostov-on-Don, "Fenix", 2008, pp. 384-385.

* cited by examiner

COSMETIC SKIN REJUVENATION

RELATED APPLICATIONS

This application is a continuation application of U.S. application Ser. No. 15/422,557, filed Feb. 2, 2017, which is a divisional application of U.S. application Ser. No. 13/388,521, filed Feb. 2, 2012, now U.S. Pat. No. 9,596,920, issued on Mar. 21, 2017, which is a U.S national stage application of PCT Application Serial No. PCT/IL10/00583, filed Jul. 21, 2010, which claims the benefit of priority from U.S. Provisional Application No. 61/231,033 filed Aug. 4, 2009. The entire contents of these disclosures are hereby incorporated by reference in their entirety.

FIELD OF THE INVENTION

The present invention relates generally to skin rejuvenation for cosmetic purposes and more specifically to performing skin rejuvenation through the use of electromagnetic energy.

BACKGROUND OF THE INVENTION

Skin is the primary barrier that withstands environmental impact on a person's body. The environmental impact results from elements such as sun, cold, wind, humidity and other conditions. The environmental factors along with aging cause the skin to lose its youthful look and develop wrinkles. This phenomenon is known as skin aging.

FIG. 1 is a schematic illustration of a side sectional view of a piece of human skin 100 and its underlying layers. Human skin 100 is made up from the epidermis 20, which is about 100 µm thick including its outermost layer the stratum corneum 10. The epidermis is followed by the dermis 30, which may extend up to about 4 mm from the surface. Subcutaneous layer 40 is located under dermis 30. These three layers control the overall external appearance of the skin (e.g. youthful or aged). The dermis 30 is made up of elastin, collagen 70, glycosoaminoglycans, and proteoglycans. The subcutaneous layer 40 includes fatty areas with fibrous vertical bands that course through it and form a link between dermal collagen 70 and subcutaneous layer 40. Collagen 70 provides the resilience and elasticity to skin. Age and sun exposure, reduce fibroplast metabolism and cause the collagen 70 to lose their elasticity and tensile strength, so that the skin loses its youthful, tight appearance.

Below subcutaneous layer 40 are located muscles 50 and muscle nerves that also contribute to the wrinkled appearance of the skin with age.

Numerous techniques have been described for skin rejuvenation by counteracting the above phenomenon, for example:

The most popular and widely used treatments for skin rejuvenation are dermabrasion peels, laser peels and chemical peels. These types of peels cause mild injury to the skin that is not too deep but yet deep enough to induce healing. The skin with its natural ability to repair itself initiates a process of rejuvenation thereby repairing the damage caused and improving the cosmetic appearance.

Dermabrasion is a method of removing skin by way of polishing or sanding. Once the old skin is abraded, a fresh layer of skin replaces the old one which has been removed.

In chemical peeling, a chemical solution is applied to the skin thus prompting the upper most layer of skin to peel off. Once the old layer of skin is removed a fresh layer of skin, which is better in color and blemish free, is formed replacing the peeled off layer. Different types of chemical peels enable achieving mild, moderate or deep peels suitable for different patients needs. A mild peel is a procedure that removes the superficial skin layer. This chemical peel involves a diluted acid solution, which normally stays on the skin for a few minutes. The Medium Peel procedure goes a little beyond the superficial layer of the skin. The chemical solution, as compared to mild peels, is kept on the skin for a longer time. Unlike the mild and medium-depth peel, a deep chemical peel penetrates deeper in the dermal layer to address more pronounced skin pigmentations and wrinkles.

One major disadvantage of these peeling methods is that after any peel and during the healing process, the treated area may become crusted resulting in skin pigmentation problems. Thus difficulties to control the depth of the peeling, possible pigment change, and risk of scarring are among the risks associated with chemical peeling.

The above mentioned methods suffer from being invasive and involving significant discomfort, pain, downtime and potential side effects. As these cosmetic procedures are all elective procedures, pain and the occasional side effects have been a significant deterrent to many potential customers, who would otherwise like to deal with skin problems.

To overcome some of the issues associated with the invasive procedures, laser and radio frequency energy based wrinkle reduction treatments have been proposed. For example, U.S. Pat. No. 6,387,089 describes a procedure referred to as photo rejuvenation, wherein pulsed light is used for heating and shrinking the collagen and thereby restoring the elasticity of the skin. Since collagen is located in the dermis, lasers that target collagen must penetrate through the epidermis and through the dermal epidermal junction. Due to Bier's Law of absorption, the laser beam is typically most intense at the surface of the skin. This results in unacceptable heating of the upper layers of the skin. Various approaches have been described to cool the upper layers of the skin while maintaining the layers underneath at the desired temperature. One approach is to spray cryogen on the surface so that the surface remains cool while the underlying layers (and hence collagen) are heated. Such an approach is described in U.S. Pat. No. 6,514,244. Another approach described in U.S. Pat. No. 6,387,089 is the use of a cooled transparent substance, such as ice, gel or a crystal that is in contact with the surface of the skin. The transparent nature of the coolant would allow the laser beam to penetrate the different skin layers while maintaining an acceptable temperature level on the surface of the skin.

Photo rejuvenation requires the use of intense pulses of filtered light. The light penetrates the outer skin layers, causing them minimal damage, and is absorbed by deeper tissues. Photo rejuvenation is useful only in treating fine to moderate wrinkles.

Photo rejuvenation risks include swelling, scarring, blistering, hyper/hypo pigmentation, sensitivity to sun exposure and sensitivity to make-up. Individuals with darker skin tones may suffer from hyper pigmentation for several months following treatment. During the recovery stage sun exposure must be avoided to minimize side effect such as hyper pigmentation.

Extensive sun exposure may lead to chronic UV irradiation. This appears to trigger dysfunctional wound repair pathways in the skin that involve gradual replacement of normal epidermal and dermal structures with characteristic atrophy and accumulation of elastotic dermal matrix components.

Currently, reversal of photo-aging is attempted by imparting cutaneous injury that induces new dermal collagen formation. Such cutaneous injury could be accomplished using mechanical (e.g., dermabrasion), chemical (e.g., retinoids and acid peels), or laser treatments. These cutaneous injuries are expected to initiate normal fibro-proliferative responses of the upper reticular and papillary dermal compartments, resulting in rejuvenated skin. U.S. Pat. No. 6,120,497 describes thermally injuring collagen in the targeted dermal region to activate fibroblasts. The fibroblasts in turn deposit increased amounts of extracellular matrix constituents. However, epidermal injury associated with a mechanical surface ablation process such as dermabration or peeling. Promotes the inflammatory phase, which inhibits the rejuvenative process. Hence, while the currently used methods, which are mentioned above, for initiating normal fibro-proliferative response of the dermal compartments can yield rejuvenated skin, due to the epidermal injury that occurs with these processes, the rejuvenative process is compromised.

An objective of nonablative photorejuvination is to induce a thermal wound repair response in the papillary and upper reticular dermal compartments (approximately 100-400 μm below the surface of the skin) while sparing the epidermal compartment. To spare the epidermis, one typically uses low fluences (laser energy densities). Unfortunately, such low levels are generally inadequate to promote the kinds of stimulation that are required to cause the desired dermal effect. Thus, prior art approaches result in low efficacy. In most cases, low dermal matrix remodeling and clinical responses (e.g., wrinkle reduction, retexturing, dyschromia reduction, and telangiectasia removal) are achieved by these procedures. Thus there is an unmet need for sparing the epidermal layer, but achieving enough stimulation of dermal matrix remodeling to be clinically effective.

To overcome some of the problems associated with the undesired heating of the upper layers of the skin (epidermal and dermal), U.S. Pat. No. 6,311,090 describes using RF energy and an arrangement comprising RF electrodes that rest on the surface of the skin. A reverse thermal gradient is created that apparently does not substantially affect melanocytes and other epithelial cells. However, even such non-invasive methods have the significant limitation that energy cannot be effectively focused in a specific region of interest, say, the dermis 30.

Electrosurgical resurfacing involves the use of a microelectrical radio frequency that delivers energy to the skin. This treatment can be effective in eliminating or improving minor to moderate skin imperfections.

Other approaches have been described to heat the dermis without heating more superficial layers. These involve using electrically conductive needles that penetrate the surface of the skin into the tissue and provide heating. U.S. Pat. Nos. 6,277,116 and 6,920,883 describe such systems. Unfortunately, such an approach results in widespread heating of the subcutaneous layer and potentially melting the fat in the subcutaneous layer. This leads to undesired scarring of the tissue.

One approach that has been described to limit the general, uniform heating of the tissue is fractional treatment of the tissue, as described in U.S. Patent Application publication No. 2005/0049582. This application describes the use of laser energy to create treatment zones of desired shapes in the skin, where untreated, healthy tissue lies between the regions of treated tissue. This enables the untreated tissue to undergo a healing and recovery process.

As opposed to traditional laser resurfacing, which treats the whole surface of the target tissue, fractional laser skin resurfacing uses fractional Photothermolysis. It targets tissue with a pattern of dispersed spots. This results in a pattern of microscopic zones of tissue coagulation that heal over several weeks while the skin retains normal appearance. Rather than creating a global tissue effect at the surface of the target tissue, or in the dermis alone, this method creates injury in a tiny fraction of the skin treated, coagulating multiple columns of tissue, 70-100 micron in diameter, extending through the epidermis and deep into the dermis reaching up to 1 mm depth. These laser columns create micro thermal zones of tissue coagulation which is surrounded by healthy tissue. The treated zone consists approximately 15-20% of the surface. Tissue is not vaporized and the stratum corneum 10 remains intact. The healthy tissue provides a generous reservoir of stem cells and melanocytes in the papillary dermis that are spared from wounding and accelerate the healing process. The small size of the wounds and the short migratory paths for keratinocytes from the spared tissue result in rapid re-epitheliazation and fast epidermal repair. Zones of collagen denaturation in the dermis cause upregulation of the inflammatory cascade, which leads to collagen remodeling to depths of 400-700 microns resulting in skin tightening. The fact that patients do not have open wounds leads to minimal downtime. Fractional laser resurfacing is therefore a non-ablative procedure offering a gentle yet effective method for skin resurfacing at minimal patient downtime and minimum risk. It offers improved skin texture, tone, pigmentation, fine lines and skin tightening. It claims to be safe for all skin types and can be used on areas other than the face such as the neck, chest and hands which are more delicate and tend to scar. Fractional resurfacing requires a series of 3-5 treatments as opposed to ablative lasers that require a single treatment.

A disadvantage of fractional laser resurfacing is that in order to achieve dramatic results heating of the tissue reaches the temperature in the necrotic zone which is around 70° C., and the tissue, whether it is made up primarily of cells, keratinocytes and their derivatives or collagen, is necrosed or denatured, respectively. Temperatures in the tissue above 100° C. may cause steam to form in the tissue, which may cause disruptive effects. Such temperatures may result in undesirable side effects such as pain, erythema, swelling, occasional scarring, extended healing times and infection.

Thus there is an unmet need for a fractional treatment that causes tissue injury and triggers tissue healing processes but without the risks and complications caused by tissue heating that creates denaturation and coagulation of tissue.

Another method of treating wrinkles includes the use of Botox. Botox is a toxin that is injected into the patient's muscles. The toxin blocks the nerve impulses, temporarily paralyzing the muscles and causing the muscles to relax. As a result wrinkled skin is smoothed out. The smoothing effect is apparent almost immediately and improves over the next few days. Generally the effects of a Botox injection last for between 3 to 6 months depending on the severity of the wrinkles and on the dosage of Botox used.

SUMMARY OF THE INVENTION

An aspect of an embodiment of the invention, relates to an apparatus and method for cosmetically treating various internal layers of the skin to achieve improved and more youthful appearance of the skin. The method is based on the use of a needle electrode that is inserted into selected depths in a person's skin and applying a negative DC voltage to the needle. Optionally, the selected depths are below the position of the hair follicles to deal with deeper elements of skin

100 that are not dealt with by hair epilation. The DC voltage induces a cold chemical process in the cells surrounding the needle causing selective destruction of cells. The chemical process forms Sodium Hydroxide (NaOH) by electrolysis and the Sodium Hydroxide then destroys surrounding cells. In some embodiments of the invention, the apparatus further includes an RF transmitter that is coupled to the needle and positioned above the surface of the skin while applying the DC voltage, to heat the treated area and resulting solution, thereby accelerating the chemical process.

In some embodiments of the invention, the needle is hollow to allow for the provision of saline or other substances (e.g. anesthetics, lidocaine, epinephrine, growth factors, stem cells, botulinum toxin) to the position at which the DC voltage is applied to accelerate the chemical process. Optionally, the hollow needle may also serve as a suction for removing fluids.

In some embodiments of the invention, part of the needle is covered with an insulation to limit the area that is in contact with skin cells and providing negative charge, for example leaving only the tip of the needle non-insolated.

In some embodiments of the invention, the needle serves as a sensor to measure resistance, so that user can determine the skin layer located at the tip of the needle.

In an exemplary embodiment of the invention, the needle is positioned to damage muscles and muscle nerve cells, so that the muscles will become lapse and cause wrinkles to disappear. Alternatively or additionally, the needle is positioned to damage fat cells in the subcutaneous layer to reduce the thickness of the skin. Optionally, liquid formed by the damaged fat cells is removed by suction. In some embodiments of the invention, the needle is positioned to damage collagen fibers so that they may be rejuvenated. One of the advantages of the use of a needle with DC voltage is that the damage is pin pointed to the position surrounding the needle, thereby enabling precise damage to a desired area.

There is thus provided according to an exemplary embodiment of the invention, a device for cosmetic treatment of human skin, including:

a needle for inserting into the skin;

a DC power source electrically connected to the needle for providing negative current to the needle;

an anode that is electrically connected to the DC power source to receive positive current, and that is adapted to be placed in contact with the skin of the person into which the needle is inserted to form a closed electrical circuit;

at least one RF transmitter coupled to the needle for radiating the area around where the needle is inserted to provide heat while the needle is deployed.

In an exemplary embodiment of the invention, the needle is hollow to enable transfer of fluid into the skin or out of the skin while the needle is deployed. Optionally, the device includes a syringe to inject fluid through the needle. In an exemplary embodiment of the invention, the device includes a motor to control the injection of fluid from the syringe. Optionally, the device includes a resistance sensor to measure the resistance in the DC circuit responsive to the position of the needle in the skin. In an exemplary embodiment of the invention, the device is adapted to provide an indication regarding the measured resistance. Optionally, the device includes a display to provide information to a user. In an exemplary embodiment of the invention, the device includes one or more dials to accept information from a user. Optionally, the device is adapted to automatically control the timing of the provision of DC current and RF radiation. Optionally, the timing is user selectable. In an exemplary embodiment of the invention, the device is adapted to provide DC current and RF radiation simultaneously. Alternatively, the device is adapted to provide DC current and RF radiation intermittently. Optionally, the needle is partially insulated. In an exemplary embodiment of the invention, only the tip of the needle is not insulated.

In an exemplary embodiment of the invention, the device includes an array of needles for inserting into the skin and serving as cathodes charged with current from the DC power source. Optionally, all the needles are provided with the same current. Alternatively, some of the needles are provided with a different current than the others. In an exemplary embodiment of the invention, the device includes an AC current source to generate the RF radiation.

There is further provided according to an exemplary embodiment of the invention, a method of treating skin, including:

deploying a needle to a specific depth into a persons skin below the roots of the person's hair follicles;

applying a negative DC voltage to the needle, while the person is in contact with a positive electrode to form a closed circuit of DC current through the person's body;

providing DC current for a pre-selected amount of time to induce a chemical reaction that forms Sodium Hydroxide at the point of contact of the needle.

In an exemplary embodiment of the invention, the method includes transmitting RF radiation toward the deployed needle to heat up the deployed area. Optionally, the transmitting and the providing are performed simultaneously. Alternatively, the transmitting and the providing are performed intermittently. In an exemplary embodiment of the invention, the method includes supplying liquids into the skin through a hollow conduit in the needle. Optionally, the deploying is of an array of needles. In an exemplary embodiment of the invention, the method includes measuring resistance of the circuit to determine the depth of the needle. Optionally, the method includes providing an indication of the depth to the user. In an exemplary embodiment of the invention, the needle is deployed so that its tip is located in the vicinity of the muscles below the subcutaneous layer. Alternatively, the needle is deployed so that its tip is located in the vicinity of the collagen fibers in the dermis. Further alternatively, the needle is deployed so that its tip is located in the vicinity of fat cells in the subcutaneous layer. Optionally, the resistance is measured before and after treatment to determine the level of success of the treatment.

BRIEF DESCRIPTION OF THE DRAWINGS

The present invention will be understood and better appreciated from the following detailed description taken in conjunction with the drawings. Identical structures, elements or parts, which appear in more than one figure, are generally labeled with the same or similar number in all the figures in which they appear, wherein.

DETAILED DESCRIPTION

Figure 1:
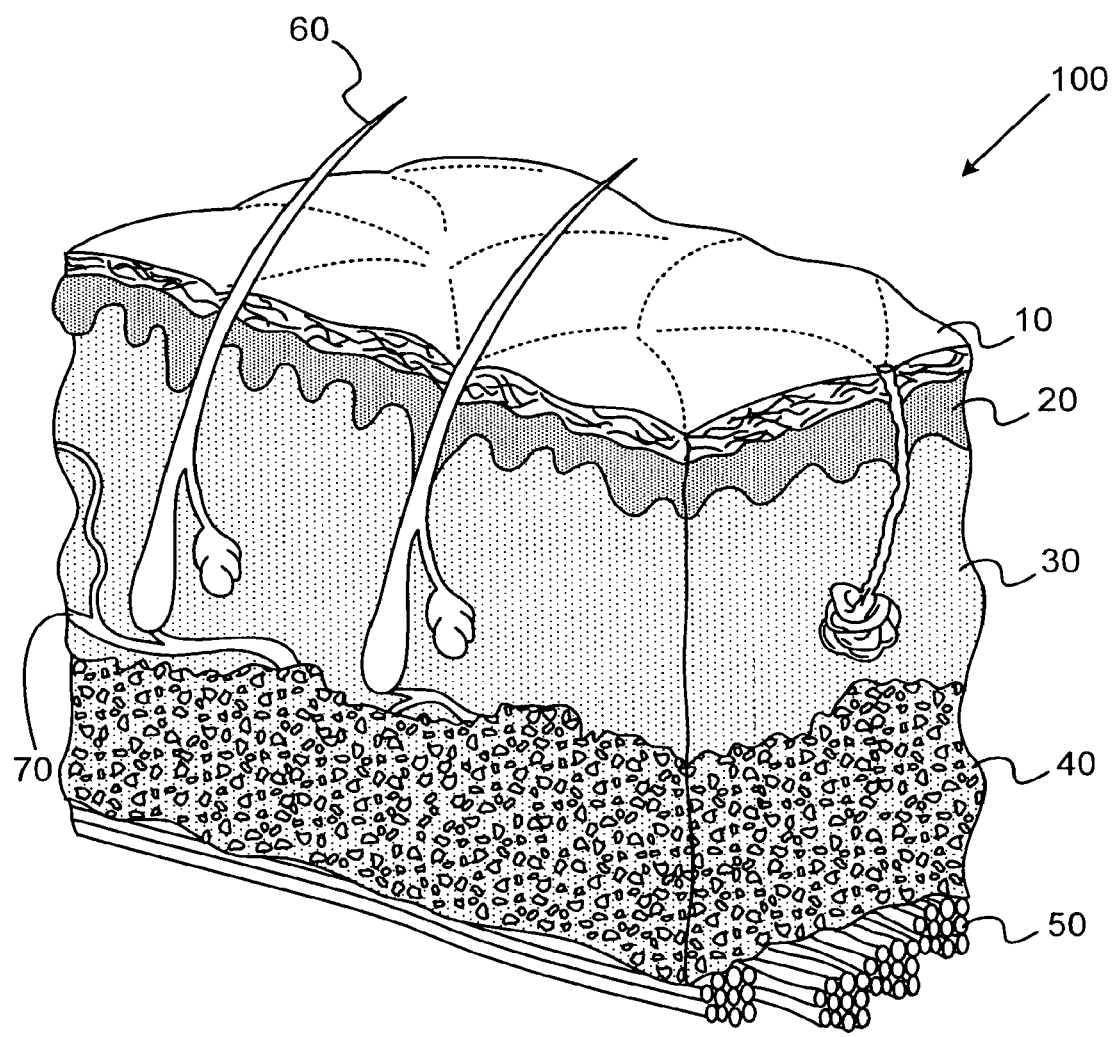
FIG. 1 is a schematic illustration of a side sectional view of skin and underlying layers.
Figure 2:
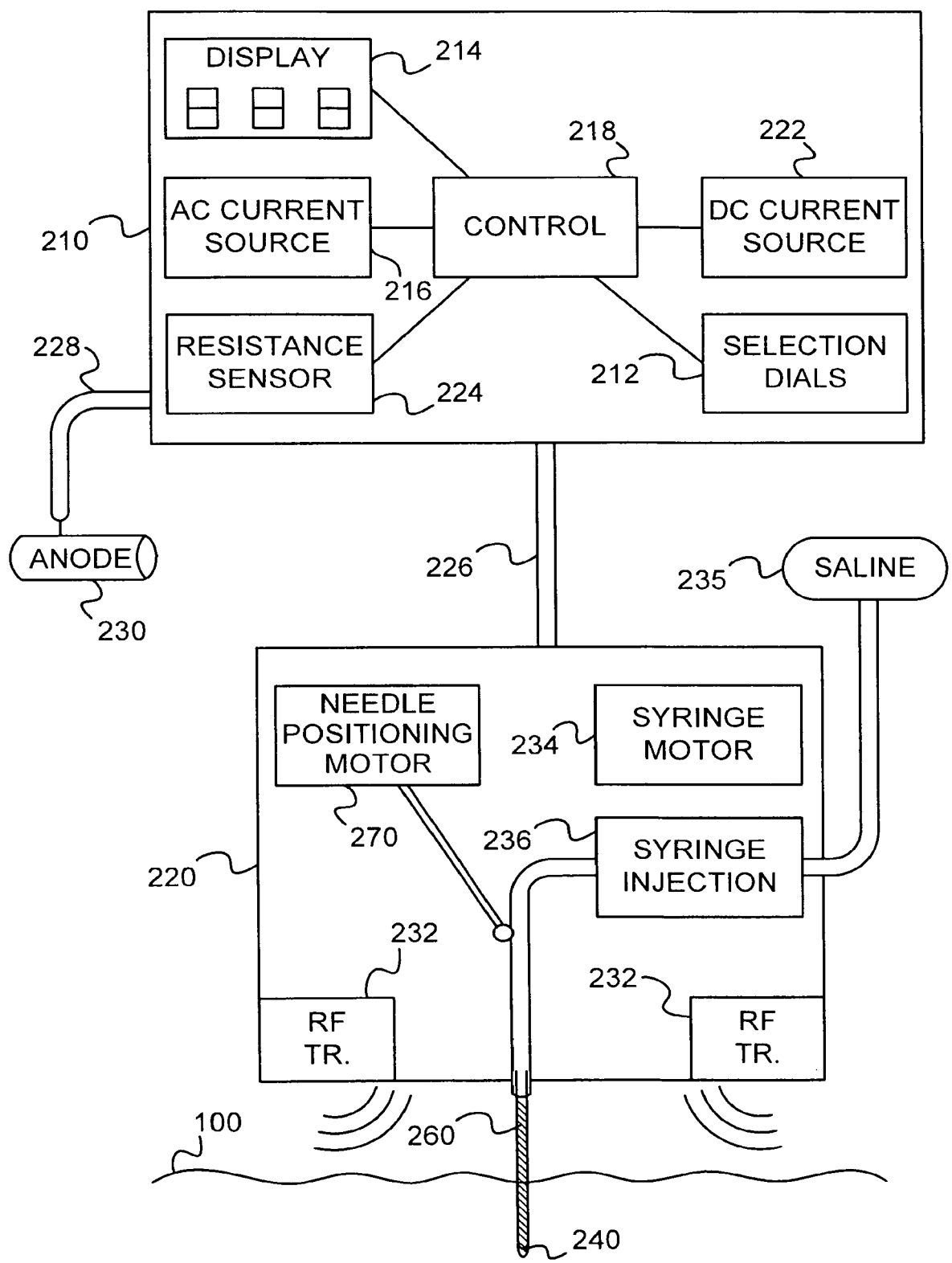
FIG. 2 is a schematic illustration of a device for treating skin, according to an exemplary embodiment of the invention.

FIG. 2 is a schematic illustration of a device 200 for treating skin 100, according to an exemplary embodiment of the invention. In an exemplary embodiment of the invention, a negative electrode of a DC circuit is provided as a needle 240 in device 200. The needle 240 is adapted to be inserted into the skin 100 of a person for performing electrolysis. Optionally, the needle has a small diameter, for example between 50-500 microns so that it does not cause noticeable damage to the outer layer of the skin when inserted into the skin.

A person's skin 100 contains moisture made of water ($H_2O$) and salt (NaCl). The amount of moisture tends to rise the deeper you penetrate into the skin, for example the dermis 30 tends to be more moist than the epidermis 20 and the fatty areas in the subcutaneous layer 40 tend to be more moist than the dermis 30. The negative electric current causes some of the water and the salt molecules of the moisture to break up into Ions ($Na^+$, $Cl^-$, $H^-$ and $OH^+$). The positive Ions ($Na^+$ and $OH^+$) move towards the negative electrode and recombine to form an Alkali Sodium-Hydroxide (NaOH). The Sodium-Hydroxide is highly caustic and destroys cell tissue located in the area of needle 240 when the negative DC voltage is applied.

The amount of Sodium Hydroxide, popularly referred to as units of Lye, depends on the current intensity and on the duration of applying the current. A unit of Lye is defined as the product of applying a tenth of a milliamp of current for 1 second. The moisture content of skin 100 increases the conductivity so that if the moisture is higher current will flow faster and the production of Lye will be increased.

In an exemplary embodiment of the invention, needle 240 extends from a handpiece 220, which can be held by the user to treat the skin 100 of a person. Optionally, needle 240 is hollow forming a conduit, and handpiece 220 includes a syringe 236, which can be filled with a liquid, for example saline from an external container 235. During application of current to the needle, syringe 236 may deliver liquid through the hollow of needle 240 to its tip to enhance the chemical process. In some embodiments of the invention, handpiece 220 includes a motor 234 to control syringe 236, so that the amount of liquid can be delivered accurately, for example a drop every few seconds. In some embodiments of the invention, other materials may be delivered for various purposes, for example anesthetics, Lidocaine, Epinephrine, growth factors, stem cells, or Botulinum toxin.

In some embodiments of the invention, needle 240 is covered or coated with an insulator 260 so that the DC current will be delivered more accurately—only at the tip of needle 240. Alternatively, the DC current may be delivered by contact with skin 100 along the entire length of needle 240.

In an exemplary embodiment of the invention, handpiece 220 includes one or more RF transmitters 232 that provide a high frequency electromagnetic radiation directed toward skin 100. Optionally, when deploying needle 240 into skin 100 RF transmitters 232 are used to heat the position where the chemical process is occurring to speed up the chemical process. Optionally, RF radiation may be applied continuously to keep the area warm or may be applied simultaneously when DC voltage is applied or separately only when the DC voltage is turned off. In some embodiments of the invention, the RF radiation only provides enough heat to enhance the effectiveness of the chemical process. Alternatively, the RF radiation may provide enough heat to destroy cells on its own, for example by thermolysis using cauterization or coagulation, in addition to the chemical process that is induced by the DC voltage.

Optionally, the application of both DC voltage and RF radiation simultaneously or intermittently reduces the time required to achieve the desired result, and may reduce the required current, for example using 0.2 to 0.7 milliamp instead of 0.5 to 1 milliamp.

In an exemplary embodiment of the invention, device 200 includes an electrical unit 210 for providing electrical power and controlling the function of handpiece 220. Optionally, electrical unit 210 is coupled to handpiece 220 by way of an electrical cable 226. In an exemplary embodiment of the invention, electrical unit 210 includes a DC current supply 222 to provide regulated negative voltage to needle 240. In an exemplary embodiment of the invention, DC current supply 222 provides a constant current regardless of the load, so that the current is not affected by resistance changing during treatment.

Additionally, electrical unit 210 may include an AC current source to provide current to RF transmitters 232 or the RF transmitter may be power by DC current. In an exemplary embodiment of the invention, an anode 230 is connected by a cable 228 to electrical unit 210. Anode 230 is held by or attached to the person being treated to form a closed electrical circuit through the body of the person being treated.

In some embodiments of the invention, electrical unit 210 includes a resistance sensor that measures the resistance through the DC circuit between needle 240 that serves as the cathode, and anode 230. Optionally, the resistance value may be displayed on a display 214 or may give off audible signals (e.g. more rapid or less rapid) or other indications, so that the user of device 200 may estimate the depth of needle 240 based on the signals, since the resistance of the skin 100 differs at different depths.

In some embodiments of the invention, electrical unit 210 may include a processor or logic circuit to facilitate a control unit 218. Optionally, control unit 218 may include several programs for controlling the device and the user selects the desired program, for example by setting switches or dials 212. In some embodiments of the invention, control unit 218 is programmable. Optionally, device 200 can be connected to a computer (e.g. through an I/O port) to receive commands regarding the control of device 200.

Optionally, the functions controlled by control unit 218 may include the following:
1. Display of status details on display 214;
2. Provision of power (e.g. DC or AC) to various units of the device;
3. Controlling the syringe motor 234;
4. Controlling the provision of saline to the syringe;
5. Providing audible signals;
6. Controlling timing of the electrical signals so that they will be synchronized relative to each other.

In an exemplary embodiment of the invention, the DC signal may provide different amounts of current for different lengths of time depending upon the position being treated in the skin, for example when treating muscles and muscle nerves control 218 may apply a direct current of 1-2 milliamp for the duration of 10-30 seconds, whereas when treating fat in the subcutaneous level a direct current of 0.1-0.8 milliamps for 5-15 seconds may be used.

In an exemplary embodiment of the invention, handpiece 220 includes a needle positioning motor 270. Optionally, needle positioning motor 270 automatically positions the X-Y-Z coordinates of the needle relative to handpiece 220, so that the needle can be accurately and automatically controlled when handpiece 220 is held stationary. The use of needle positioning motor 270 allows better accuracy than achievable by a practitioner moving handpiece 220 manually.

Figure 3:
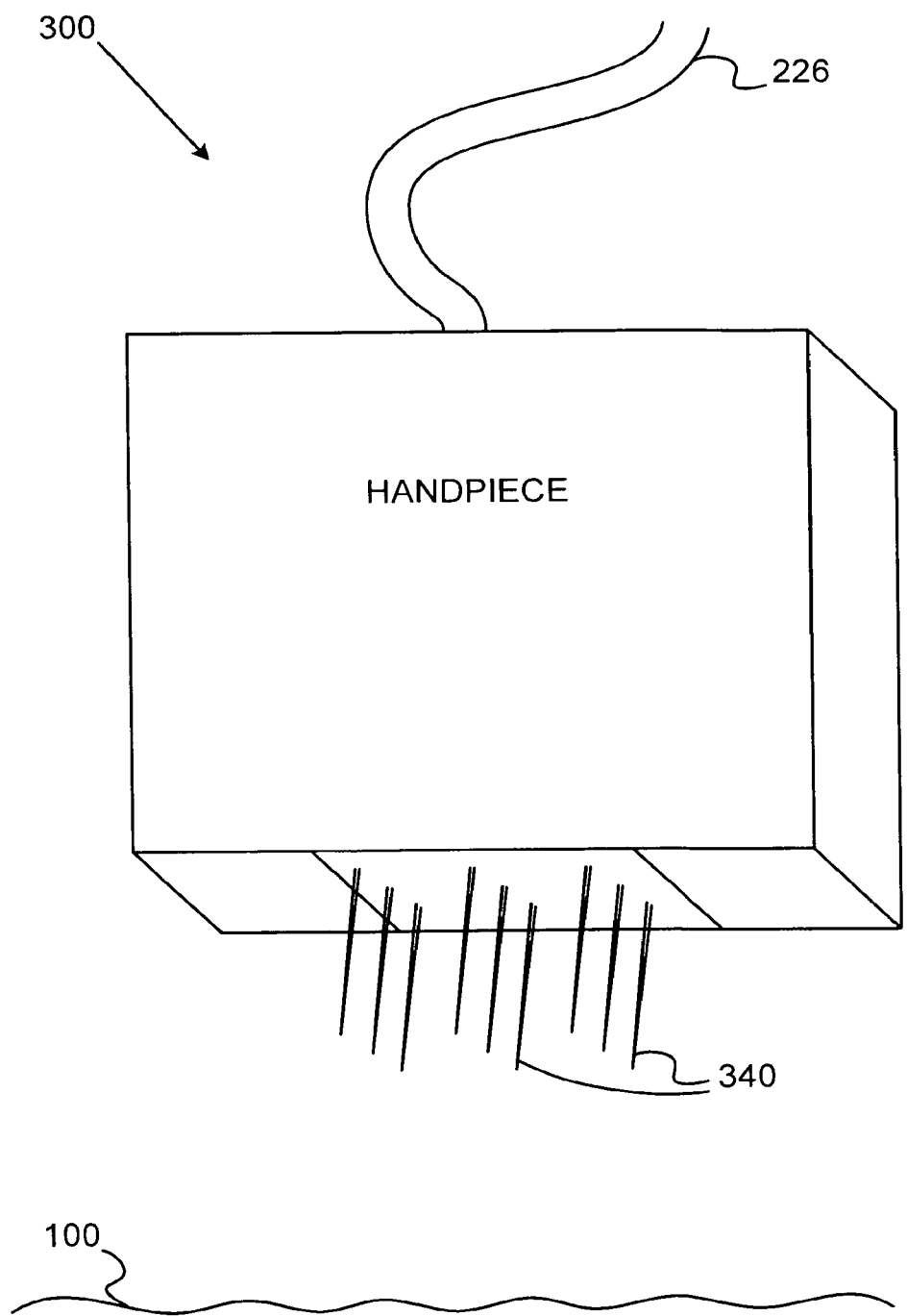
FIG. 3 is a schematic illustration of an alternative handpiece with an array of needles, according to an exemplary embodiment of the invention.

In an exemplary embodiment of the invention, more than one needle 240 may be used to increase the number of points that are treated simultaneously. FIG. 3 is a schematic illustration of an alternative hand piece 300 with an array of needles 340, according to an exemplary embodiment of the invention. Optionally, array 340 may be provided in any shape and with any number of needles. Optionally, the needles may be equally spaced or unequally spaced. Additionally, the needles may form a symmetrical pattern or a non-symmetrical pattern. In some embodiments of the invention, each needle may be controlled separately or groups of needles from the array may be controlled together to form specific treatment patterns.

Figure 4:
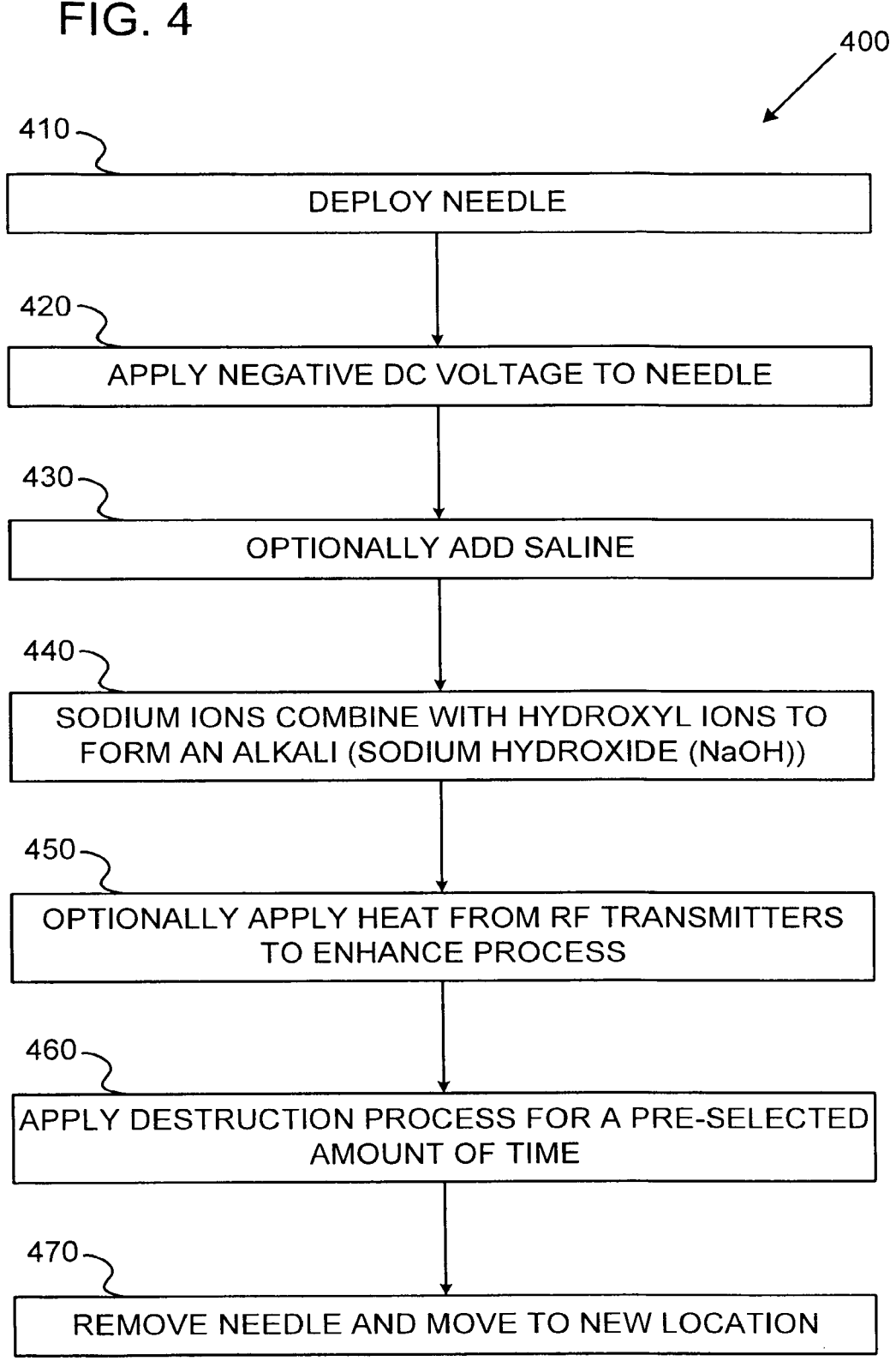
FIG. 4 is a flow diagram of a cosmetic skin treatment process, according to an exemplary embodiment of the invention.

FIG. 4 is a schematic illustration summarizing a cosmetic skin treatment process 400 using device 200, according to an exemplary embodiment of the invention. As shown in FIG. 4 initially the user deploys (410) needle 240 to the desired depth in a person's skin 100. The desired depth may depend on the type of treatment being performed and/or on the area of the body being treated, for example epidermis 20 in the face and neck is 100 microns thick and dermis 30 is 1900 microns thick. In other parts of the body the epidermis and dermis may be thicker or less thick than these values. Optionally, needle 240 is designed to allow penetration of about 1-12 mm. Optionally, device 200 provides the user with an indication of the position in the skin 100 based on the measured resistance between the cathode and the anode. Alternatively or additionally, the user is required to recognize the depth to which needle 240 is deployed based on human anatomy. Once needle 240 is positioned the user may apply (420) a negative DC voltage to needle 240 for a pre-selected length of time with a pre-selected level of current, for example the voltage may be between 1 to 40 Volts, current between 0.1 to 1 milliamp and time may be between 1 to 1 to 30 seconds. In an exemplary embodiment of the invention, the user sets selection dials 212 to select the desired parameters and have them applied automatically and accurately by device 100 when pressing an activation button after deploying needle 240.

In an exemplary embodiment of the invention, the penetration depth is determined by measuring the current or resistance of the circuit, since the resistance varies depending on the penetration depth or tissue layer. In some embodiments of the invention, the resistance is measured before treatment and after treatment to determine the level of success in damaging the targeted area.

In an exemplary embodiment of the invention, the parameters applied during the treatment depend upon many attributes, for example:
1. The type of skin flaw being treated (e.g. stains, wrinkles, scars, keloids, fat, tattoos);
2. The tolerance to pain of the person being treated;
3. The skin and tissue sensitivity of the person being treated;
4. The area being treated;

Optionally, the user may instruct device 200 to add Saline (430) or other liquids to enhance the success of the treatment. The DC voltage causes electrolysis to take place at the point of contact of needle 240 in the person's skin 100. The electrolysis releases Sodium and Hydroxyl Ions that are attracted to needle 240 causing them to combine and form (440) an Alkali: Sodium Hydroxide (NaOH). The Sodium Hydroxide is caustic and destroys cells surrounding the point of contact. The Sodium Hydroxide will be formed as a drop at the tip of the needle or along the non-insulated length of the needle. As a result the process causes precise damage to the selected layer below the surface of skin 100 without leaving noticeable markings on the outer layer of skin 100.

In an exemplary embodiment of the invention, device 200 includes RF transmitters that produce radiation directed toward the area being treated causing heat to be applied (450) to the area being treated. Optionally, the RF transmitters transmit at frequencies between the range of 0.5 to 40 Mhz so that the radiation is felt as heat in the person's skin 100. Optionally the heat accelerates the production of Sodium Hydroxide and/or assist in destroying cells surrounding the point of contact.

In an exemplary embodiment of the invention, the destruction process is applied (460) for a pre-selected amount of time (e.g. based on the size of the area needed to be ablated). Optionally, needle 240 may be used as a suction to remove (470) unwanted fluids, for example melted fat. After treating a specific area the user may remove (480) the needle and move it to treat a new location. Optionally, if using array 340 a larger area may be treated simultaneously instead of a single point. In some cases it may be advantageous to quickly cover a larger area, although in other cases pin point accuracy may be desired.

In some embodiments of the invention, needle positioning motor 270 controls the movement of each needle or a group of needles. Optionally, needle positioning motor 270 is programmed to treat a specific area while automatically controlling the spatial (X-Y-Z) coordinates of needle 240.

Figure 8A:
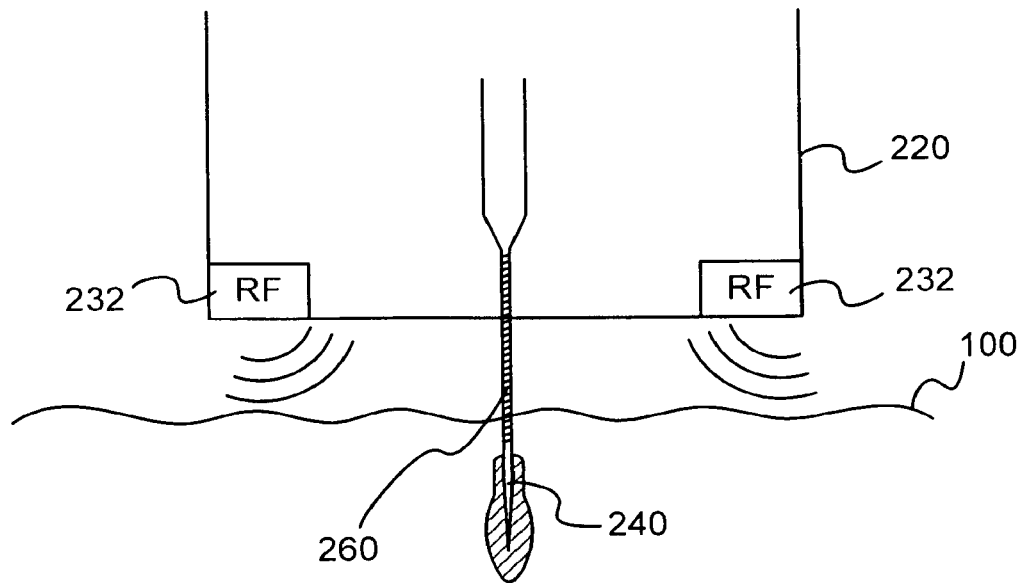
FIG. 8A is a schematic illustration of a single injection needle performing electrolysis, according to an exemplary embodiment of the invention.
Figure 8B:
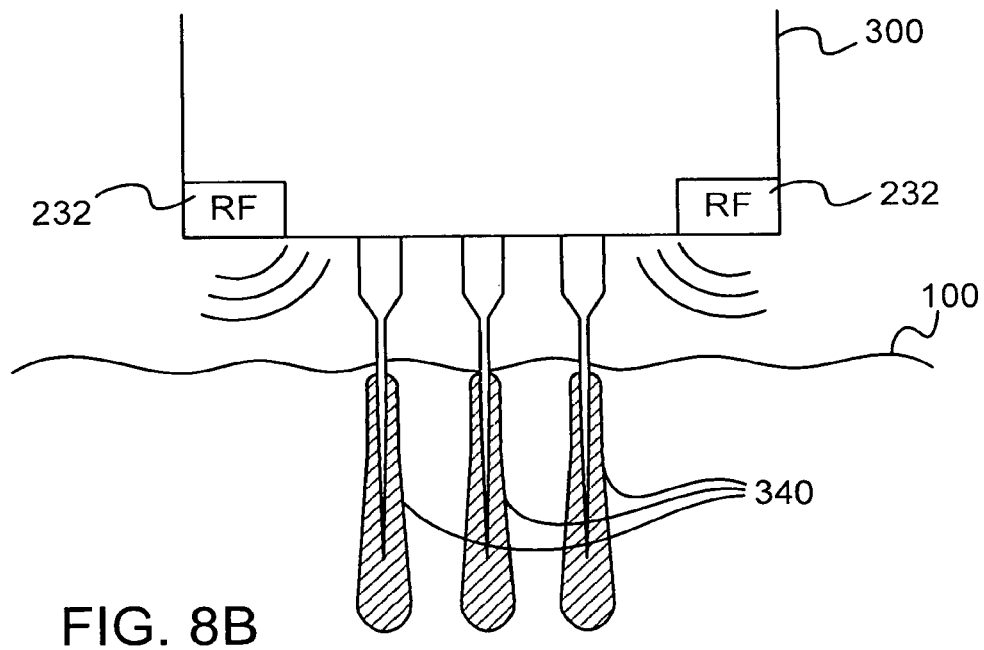
FIG. 8B is a schematic illustration of an array of injection needles performing electrolysis, according to an exemplary embodiment of the invention.

FIG. 8A is a schematic illustration of a single injection needle 240 performing electrolysis, according to method 400 as described above. FIG. 8B is a schematic illustration of an array of injection needles 340 performing electrolysis, according to method 400 as described above. In FIG. 8A needle 240 is covered with an insulation 260 and the chemical process is limited to the non-insulated area at the tip of needle 240. In contrast in FIG. 8B the needles of array 340 are not insulated so the chemical process occurs along the length of the needles in the skin, limited by the moisture gradient, wherein the deeper layers are moister than the upper layers so that more Sodium Hydroxide forms at the lower layers.

In some embodiments of the invention, device 200 and process 400 is applied to the ablation of muscles 50 and muscle nerve cells, for example as a substitute to using Botox to remove wrinkles from a person's forehead or from other places on the face or body of the person. Optionally, damaging muscles 50 and muscle nerve cells will have the effect of causing muscle 50 to lapse, like when using Botox but without the need to apply toxic materials. Alternatively or additionally, Botox may be applied (e.g. through the hollow of needle 240), for example in a smaller amount, while using the above process. Optionally, Botox may be applied in addition to the application of Saline. In some embodiments of the invention, other materials may be used for example medication to prevent infection.

Figure 5:
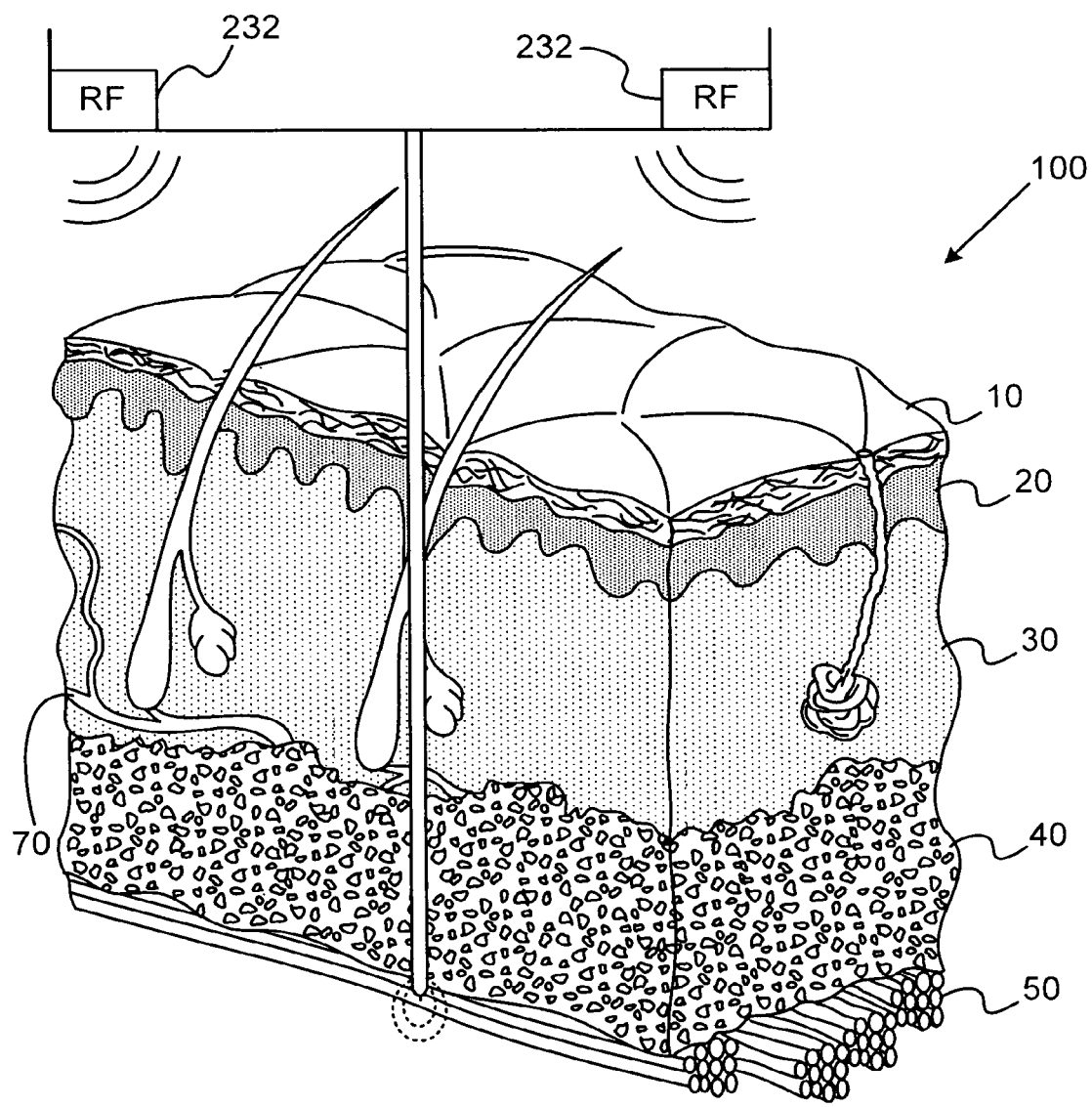
FIG. 5 is a schematic illustration of a side sectional view of skin with a needle deployed for treating muscles below the subcutaneous layer, according to an exemplary embodiment of the invention.

FIG. 5 is a schematic illustration of a side sectional view of skin 100 with needle 240 deployed for treating muscles 50 below the subcutaneous layer 40, according to an exemplary embodiment of the invention.

In some embodiments of the invention, device 200 and process 400 may be applied to the reduction of fat cells from the subcutaneous layer 40. Optionally, needle 240 may be used without insulation 260 or with less insulation to expand the area that is affected by the DC current. Optionally, this process may be used to perform liposuction. In an exemplary embodiment of the invention, needle 240 is positioned in the person's skin 100 and used to melt down fat cells. The fat cells are emulsified into an oily liquid substance, and are disposed of by the natural body waste disposal processes. Optionally, the hollow of needle 240 is used to suck out the melted cells. In some embodiments of the invention, the hollow of needle 240 is used to inject medication, for example a Tumescent solution that consists of Lidocaine and Epinephrine. Lidocaine serves as a local anesthetic and Epinephrine leads to the constriction of blood vessels leading to less blood loss and less bruising. Optionally, the use of needle 240 with DC current may reduce the need to use medication or even cancel the need.

Figure 6:
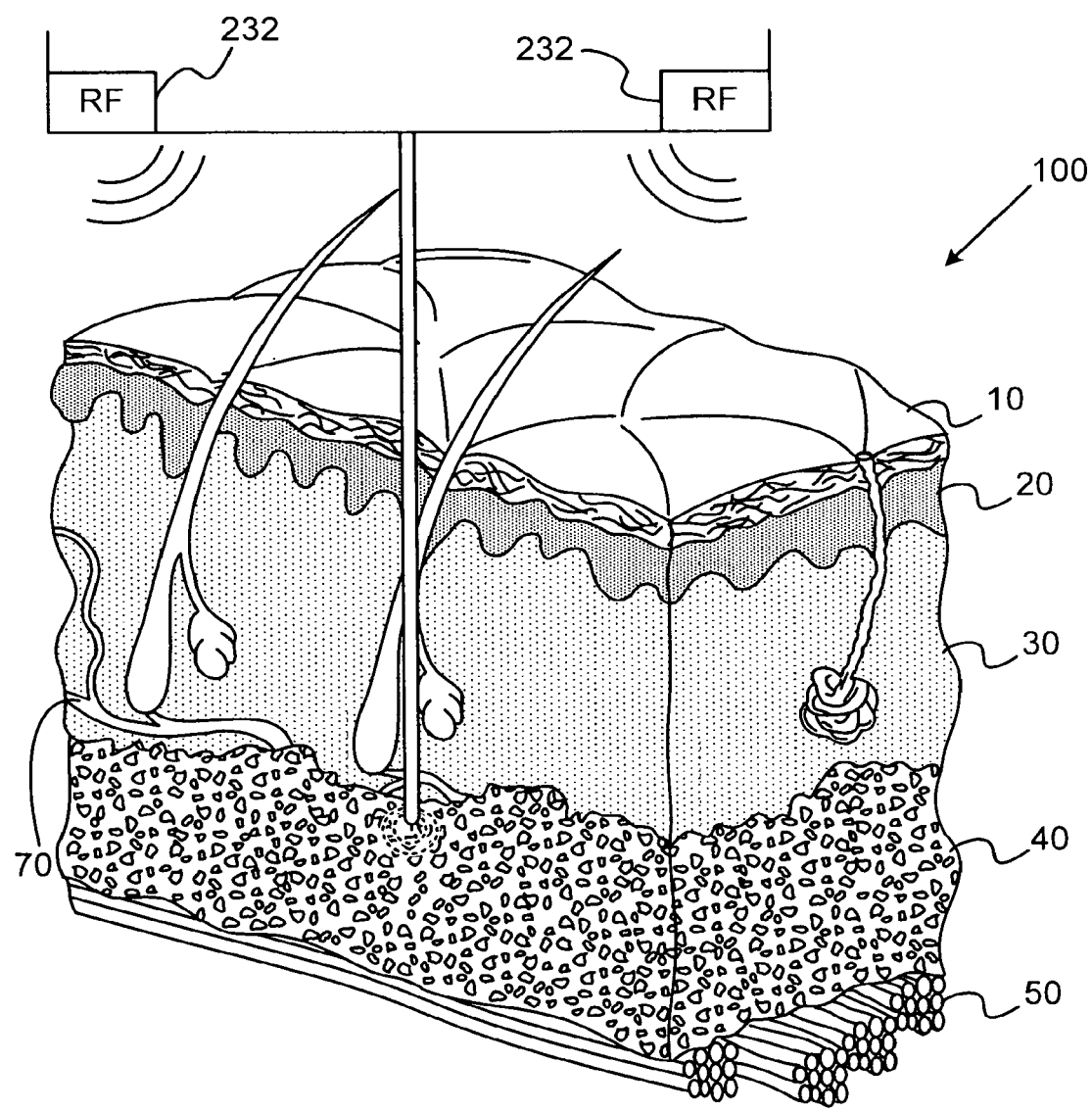
FIG. 6 is a schematic illustration of a side sectional view of skin with a needle deployed for treating fatty areas in the subcutaneous layer, according to an exemplary embodiment of the invention.

FIG. 6 is a schematic illustration of a side sectional view of skin 100 with needle 240 deployed for treating fatty areas in the subcutaneous layer, according to an exemplary embodiment of the invention.

In some embodiments of the invention, device 200 and process 400 may be applied to damage collagen fibers from the dermis 30. Optionally, needle 240 is inserted onto collagen fibers 70 and used to destroy them. The damage in the dermis 30 stimulates the body's natural healing process to produce new healthier skin 100 and collagen 70. In some embodiments of the invention, the heat produced by RF transmitters 232 results in collagen contraction leading to collagen regeneration and skin tightening. The combined effect of collagen contraction and wound healing rejuvenates skin 100. The fact that the ablation is pin pointed and the damaged areas are surrounded by healthy tissue speeds up the healing process and minimizes downtime of the person being treated.

Figure 7:
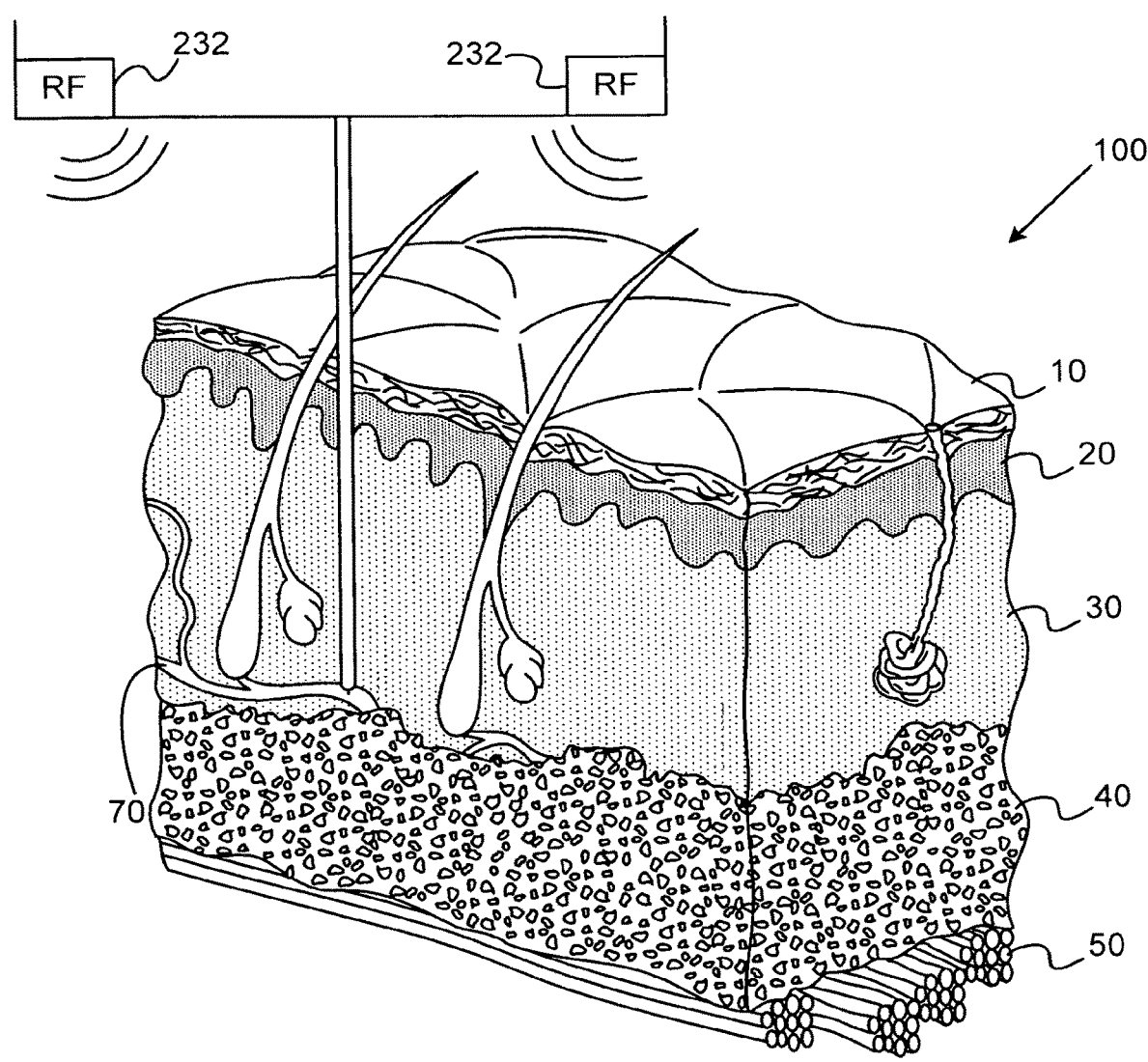
FIG. 7 is a schematic illustration of a side sectional view of skin with a needle deployed for treating collagen in the dermal layer, according to an exemplary embodiment of the invention.

FIG. 7 is a schematic illustration of a side sectional view of skin 100 with needle 240 deployed for treating collagen 70 in the dermal layer, according to an exemplary embodiment of the invention.

In an exemplary embodiment of the invention, the fact that the moisture gradient in skin tissue layers is such that moisture concentration is higher in the deeper layers minimizes the damage to the upper skin layers whether the upper part of needle 240 is covered by insulation 260 or not. Optionally, the skin surface will show no signs of the chemical process except the needle entry mark. Thus even when using the array of needles 340 or inserting needle 240 multiple times, skin 100 will show very little signs of treatment unless specifically aiming for the upper layer and using saline to enhance the process. In contrast a method that uses needles charged with AC current tends to cause excessive heating during treatment and leaves scar marks due to fat emulsification.

In an exemplary embodiment of the invention, treatment of the inner layers of skin 100 by the above methods cause the skin to become temporarily red with mild swelling but does not lead to skin peeling or require patient downtime.

In an exemplary embodiment of the invention, a number of experiments were conducted to test certain aspects of the device and methods described above.

In a first experiment the efficiency of the above method was tested by examining the effect on egg white.

An egg white of a fresh egg was placed inside a glass jar. Two electrodes were glued to two opposite inner walls of the jar. The electrodes were connected to an AC current supply generator of 1 MHz frequency and a power of approximately 5 Watt.

A third electrode was connected to the positive pole of a DC current source. This electrode was inserted into the jar. A fourth electrode was connected at one side to a needle such as used for hair removal by epilation. The needle diameter was 0.003 inch; manufactured by Ballet, model F3. The other side of the electrode was connected to the negatively charged (cathode) pole of the DC source.

In the first stage of the experiment only DC current was applied. This caused initial destruction of the egg white surrounding the needle. The time duration was measured from activation of the DC current until the formation of a white layer of dead cells around the needle.

In the second stage of the experiment, both DC and AC current were applied simultaneously. This caused initial destruction of the egg white surrounding the needle. Again, time duration was measured from the current activation until the formation of a white layer of dead cells around the needle.

The time duration measured in the first stage was found to be 2-4 times longer than the time measured in the second stage. Another observation concluded that the amount of dead cells surrounding the needle tip was significantly larger than the amount of dead cells along the needle.

In a second experiment the above methods were tested on animal tissue (flesh and fat) when applying combined currents, DC and/or AC, with or without saline solution injection.

Pork bacon slices were placed on a glass plate. A video camera was placed beneath the glass plate and the experiment was video filmed. A DC current operating at a voltage of V volts and a current intensity of A milliamp was used. A Dermatic1 mesotherapy gun from Euromi with a syringe, catheters and non-insulated needles were used to perform the experiment. The negative (cathode) electrode of the DC source was connected to the syringe needle. The positive (anode) electrode of the DC source was connected to the mesotherapy gun in order to close the electric loop. An AC current source operating at a frequency of 1 MHz and a power of W was used. The AC current was used to create an RF radiation field between two electrodes attached to the pork slice. The mesotherapy syringe needle was injected into the slice between the two AC electrodes. The mesotherapy syringe needle was injected into the slice at a penetration depth of approximately 1-2 mm for a duration time of up to 1 minute. The mesotherapy gun contained saline solution for injection into the slice.

The following scenarios were examined:
1. Syringe needle injection with no saline solution, no DC current, no AC current;
2. Syringe needle injection with no saline solution, with DC current, no AC current;
3. Syringe needle injection with saline solution, with DC current, no AC current;
4. Syringe needle injection with no saline solution, with DC current, with AC current;
5. Syringe needle injection with saline solution, with DC current, with AC current.

The following results were observed:
1. Scenario 1—No effect on slice except the forming of a needle hole.
2. Scenario 2—The DC current flowing through the needle caused a chemical reaction in the slice. A small region surrounding the needle was emulsified into oily liquid. A hole was formed in the tissue where it was emulsified. The process took approximately 1 minute. In viewing the video recording it can be seen that the initial effect is fat emulsification into liquid. In the next stage emulsification results in a small hole in the tissue which eventually grows larger and larger.
3. Scenario 3—Injection of saline solution into the slice intensified the chemical reaction. Emulsification occurred faster and on a larger scale creating a larger region of emulsification surrounding the needle. A hole was formed in the tissue where the tissue was emulsified.
4. Scenario 4—The AC current intensified the chemical reaction dramatically causing much faster emulsification and on a larger region surrounding the needle.
5. Scenario 5—Injection of saline solution into the slice intensified the chemical reaction. Emulsification occurred faster and on a larger region. A hole was formed in the tissue where the tissue had emulsified. In this scenario the effect was the most profound.

Conclusions:
The most effective method for emulsifying flesh and fat is using scenario 5 which gave the most dramatic effect. The flesh and fat should be moist. Saline solution may be injected into the treated area in order to moisten the area. The injected needle should be charged with a negative DC current and the surrounding treatment zone should be radiated by a high frequency AC signal.

It should be appreciated that the above described methods and apparatus may be varied in many ways, including omitting or adding steps, changing the order of steps and the type of devices used. It should be appreciated that different features may be combined in different ways. In particular, not all the features shown above in a particular embodiment are necessary in every embodiment of the invention. Further combinations of the above features are also considered to be within the scope of some embodiments of the invention.

It will be appreciated by persons skilled in the art that the present invention is not limited to what has been particularly shown and described hereinabove. Rather the scope of the present invention is defined only by the claims, which follow.

We claim:
1. A cosmetic method for treating a skin of a person, comprising:
inserting one or more needles to one or more depths into the skin of the person such that at least a tip of at least one needle of the one or more needles is deployed within a muscle layer of the person's skin;
providing a DC power source electrically coupled to the one or more needles;
applying a negative DC voltage to the one or more needles from said DC power source, and a positive DC voltage to an electrode in contact with a surface of the skin of the person to form one or more closed circuits of constant DC current through the person's body; and
providing the negative and positive DC current voltages having a pre-selected value for a pre-selected amount of time, the preselected value and amount of time being configured to induce a cold chemical process in the cells surrounding the one or more needles that causes selective destruction of cells including damaging and/or ablating muscles and/or muscle nerve cells in the muscle layer;
thereby providing a skin treatment comprising causing the muscles in the muscle layer to lapse and reducing and/or smoothing wrinkles from the person's skin.

2. The method according to claim 1, wherein said person's skin comprises face skin and/or forehead of the person.

3. The method according to claim 1, further comprising supplying one or more substances into the skin through a hollow conduit formed in said one or more needles to enhance the skin treatment process.

4. The method according to claim 3, wherein said one or more substances comprise one or more of the following: anesthetics, lidocaine, epinephrine, growth factors, stem cells, and botulinum toxin.

5. The method according to claim 1, further comprising measuring electrical resistance through the one or more circuits enabling to determine the one or more depths, and providing an indication of the one or more depths to the user.

6. The method according to claim 5, wherein the electrical resistance is measured before and after treatment to determine the level of success of the treatment.

7. The method according to claim 1, further comprising:
inserting at least one second needle of the one or more needles to a second depth into the skin of the person such that at least a tip of the at least one second needle is deployed within a collagen fiber region in a dermis tissue layer;
the skin treatment thereby comprising damaging the collagen fiber(s) and stimulating a natural healing process and production of new collagen fibers.

8. The method according to claim 1, further comprising:
inserting at least one third needle of the one or more needles to a third depth into the skin of the person such that at least a tip of the at least one third needle is deployed in a vicinity of fat cells in the subcutaneous layer;
the skin treatment thereby comprising melting down the fat cells and reducing fat from the subcutaneous layer.

9. The method according to claim 8, further comprising:
sucking out the melted fat cells through a hollow conduit formed in said at least one third needle.

10. The method of claim 1, wherein said one or more needles are partially insulated and the tips of the one or more needles are not insulated.

11. The method of claim 1, further comprising providing same or different respective one or more DC currents through the person's body.

12. The method according to claim 1, further comprising:
providing one or more radio frequency (RF) transmitters; and transmitting RF radiation from the one or more RF transmitters towards the treated skin of the person to thereby heat the treated skin and enhance the skin treatment.

13. The method according to claim 12, wherein said forming of the DC current and said transmitting of the RF radiation are performed simultaneously.

14. The method according to claim 12, wherein said forming of the DC current and said transmitting of the RF radiation are performed intermittently.

15. A cosmetic method for treating a face skin of a person, comprising:
   inserting one or more needles into the face skin of the person such that at least a tip of at least one needle of the one or more needles is deployed within a muscle layer of the person's face skin;
   providing a DC power source electrically coupled to the one or more needles;
   providing one or more radio frequency (RF) transmitters;
   applying a negative DC voltage to the one or more needles from said DC power source, and a positive DC voltage to an electrode in contact with a surface of the skin of the person to form one or more closed circuits of constant DC current through the person's body;
   transmitting RF radiation from the one or more RF transmitters towards the treated face skin of the person to thereby heat the treated face skin;
   and
   providing:
   the negative and positive DC voltages and the RF radiation in a pre-selected timing, the negative and positive DC voltages configured to induce a cold chemical process in the cells surrounding the one or more needles that causes selective destruction of cells, and the RF radiation configured to heat the tissue surrounding the needles, thereby damaging and/or ablating muscles and/or muscle nerve cells in the muscle layer;
   thereby providing a face skin treatment comprising reducing and/or smoothing wrinkles from the person's face skin.

16. The method according to claim 15, wherein said forming of the constant DC current and said transmitting of the RF radiation are performed simultaneously.

17. The method according to claim 15, wherein said forming of the DC current and said transmitting of the RF radiation are performed intermittently.

* * * * *